United States Patent [19]
Picatti et al.

[11] Patent Number: 6,117,085
[45] Date of Patent: Sep. 12, 2000

[54] ULTRASONIC DIAGNOSTIC IMAGING SYSTEM WITH CORDLESS SCANHEAD CHARGER

[75] Inventors: William C. Picatti, Bellevue; Leo R. Catallo, Mercer Island; Lauren S. Pflugrath, Seattle; Juin-Jet Hwang, Mercer Island, all of Wash.

[73] Assignee: ATL Ultrasound, Inc., Bothell, Wash.

[21] Appl. No.: 09/196,852

[22] Filed: Nov. 20, 1998

[51] Int. Cl.[7] ........................................................ A61B 8/14
[52] U.S. Cl. .............................................................. 600/459
[58] Field of Search .................................... 600/437, 459, 600/443, 444, 445, 446, 447, 453; 364/708.1, 725, 606, 844; 73/626; 382/128, 132

[56] References Cited

U.S. PATENT DOCUMENTS

| | | |
|---|---|---|
| 4,374,354 | 2/1983 | Petrovic et al. . |
| 4,413,629 | 11/1983 | Durley, III . |
| 5,295,485 | 3/1994 | Shinomura et al. . |
| 5,448,151 | 9/1995 | Ganse et al. . |
| 5,468,948 | 11/1995 | Koenck et al. . |
| 5,590,658 | 1/1997 | Chiang et al. . |
| 5,640,960 | 6/1997 | Jones et al. . |
| 5,685,307 | 11/1997 | Holland et al. . |
| 5,690,114 | 11/1997 | Chiang et al. . |
| 5,715,823 | 2/1998 | Wood et al. . |
| 5,722,412 | 3/1998 | Pflugrath et al. . |
| 5,851,186 | 12/1998 | Wood et al. ............................ 600/437 |
| 5,865,733 | 2/1999 | Malinouskas et al. . |
| 5,882,300 | 3/1999 | Malinouskas et al. . |
| 5,964,709 | 10/1999 | Chiang et al. ........................... 600/447 |

FOREIGN PATENT DOCUMENTS

| | | |
|---|---|---|
| 0 762 142 A1 | 8/1996 | European Pat. Off. . |
| 0 875 203 | 11/1998 | European Pat. Off. . |
| 55-151952 | 11/1980 | Japan . |
| WO 96/32888 A1 | 10/1996 | WIPO . |

Primary Examiner—Marvin M. Lateef
Assistant Examiner—Ali M. Iman
Attorney, Agent, or Firm—W. Brinton Yorks, Jr.

[57] ABSTRACT

An ultrasonic diagnostic imaging system is provided with cordless scanheads which wirelessly transmit ultrasonic image signals to the imaging system. The cordless scanheads are battery powered by rechargeable batteries which are recharged by the ultrasound system when the scanheads are not in use. In preferred embodiments the charging system is protected from contaminants such as ultrasonic gel.

14 Claims, 10 Drawing Sheets

ULTRASONIC DIAGNOSTIC IMAGING SYSTEM WITH CORDLESS SCANHEAD CHARGER

This invention relates to ultrasonic diagnostic imaging systems and, in particular, to ultrasonic diagnostic imaging systems in which the scanning of patients is done by rechargeable cordless scanheads.

Ultrasonic diagnostic imaging systems have traditionally been thought of as having two major constituent parts: a probe or scanhead, and the mainframe processor or system. The probe contains the piezoelectric transmitter and receiver of ultrasonic energy which is used to scan the patient's body. The system contains the sophisticated electronic controllers and processors which control the probe and turn the received echo signals into diagnostic images and information. But there is one additional ever-present component: the cable which connects the probe to the system, through which power and signals are coupled between the probe and system.

The probe cable has taken many forms as it has evolved over the years, and has had varying impacts on physician and patient comfort and convenience. Early products which only were used for audio Doppler or A-line (single line) imaging needed very few wires in the cable. Since the probes for such products generally used single element or single piston transducers, sometimes referred to as "pencil probes," signal and ground wires often sufficed as a complete cable. Such a probe had an unsteered, fixed focus along a single beam. The user adjusted the probe by physically moving it to a different position or offsetting it from the body with an acoustic standoff. While the thin, light cable was convenient to lift and maneuver, the caliber of the diagnostic information obtained was minimal.

The advent of B arm systems took convenience in a different direction. In these systems the probe was attached to the end of an articulated arm which provided probe position information for two dimensional imaging. The step-up in diagnostic image quality was at the expense of the articulated arm, which constrained imaging to its range of movement. Merged into the articulated arm, the cable was virtually unnoticeable in the ungainly mechanism.

Greater freedom of movement returned with the development of the mechanical sector scanner probe. The mechanical sector scanner oscillated the transducer back and forth to scan the image field, and the oscillating mechanism provided the spatial orientation for two dimensional imaging. A single piston transducer with two wires, signal and ground, was needed, as well as wires to power and control the oscillating mechanism and send the spatial orientation signals to the system. The hand-held probe was convenient, but the cable was beginning to grow in size.

Cable growth accelerated considerably with the advent of solid-state or array probes. In the array probes the transducer comprises an array of dozens or hundreds of elements which are individually controlled to electronically steer and focus the ultrasound beam. But with individual control comes the need for individual wires: a 128 element transducer probe can require a cable with 128 individual wires. Since received echo signals are generally of very low levels, the wires are not simply stranded wires, but coaxial lines, each with its own signal line and conductive shield. While various multiplexing schemes in the probe have been used to reduce the number of wires in the cable, these schemes can have adverse consequences for performance criteria such as frame rate, aperture size, and control complexity. Accordingly it would be desirable to reduce the size of the probe cable, or even eliminate it, thereby improving clinician and patient convenience but without incurring any performance penalties.

In accordance with the principles of the present invention, an ultrasonic diagnostic imaging system is presented in which the probe cable is eliminated, giving rise to the utmost convenience for the clinician and patient. This convenience is brought about by the inclusion of a wireless transmitter in the probe case, eliminating the need to connect the probe to the mainframe ultrasound system. The ultrasound system includes a receiver for receiving the ultrasound information from the probe. The cordless scanhead includes a rechargeable battery which is recharged by the ultrasound system when the scanhead is not being used for scanning. In several of the illustrated embodiments the battery recharging arrangement is protected from contamination by substances such as ultrasonic gel.

Figure 1:
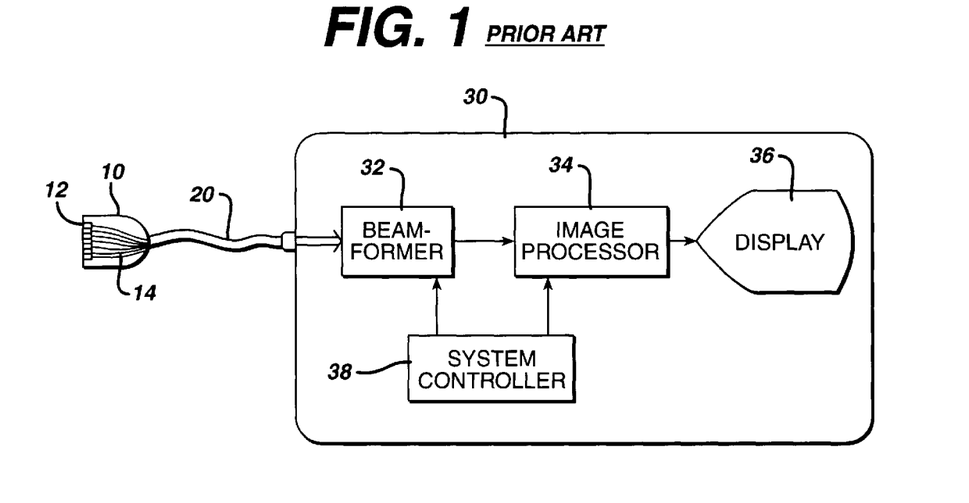
FIG. 1 illustrates in block diagram form the conventional configuration of an ultrasonic probe, cable, and ultrasonic imaging system.

Referring first to FIG. 1, a conventional ultrasonic probe, cable and imaging system arrangement is shown in block diagram form. The ultrasonic probe 10 includes a transducer array 12. Conductors 14 connect individual elements of the transducer array to conductors inside a cable 20, which connects to an ultrasonic imaging system 30. The conductors of the cable are electrically connected to a beamformer 32 in the imaging system, which controls the timing of the pulsing of the elements of the transducer array, and delays and sums received echo signals from the transducer elements to form coherent beams of echo signals. The beamformed echo signals are coupled to an image processor 34 where they are processed to form an image of tissue or flow within the body of the patient being scanned. The resultant ultrasonic image is displayed on an image display 36. Coordination of the processing and data flow of the beamformer 32 and image processor 34 is provided by a system controller 38, which receives instructions from a user by way of various user controls.

While the elements of the transducer array 12 are shown directly wired to the conductors of the cable in FIG. 1, multiplexers can be included within the probe between the array elements and the cable to reduce the number of cable conductors. It is then necessary to control the multiplexers from the ultrasound system with control lines, so that the cable conductors are multiplexed to the elements of the current active aperture each time the probe is transmitting or receiving ultrasonic signals.

Figure 2:
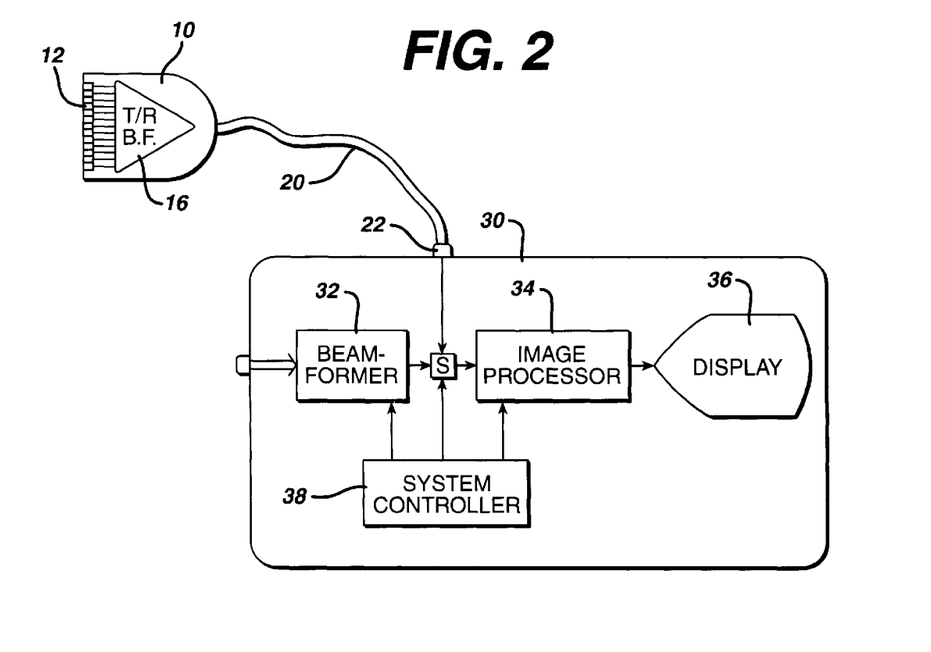
FIG. 2 illustrates an ultrasonic probe with an integral beamformer operatively connected to an ultrasonic imaging system.

FIG. 2 illustrates an ultrasound system in which the beamforming for both ultrasonic transmission and reception is done within the probe, significantly reducing the number of conductors needed within the cable 20. The elements of the transducer array 12 are coupled to a transmit/receive beamformer 16, which controls the timing, steering and focusing of the ultrasonic beams transmitted by the array and the beamforming of coherent echo signals from the signals received by the array elements. The formed beam, rather than signals from each transducer element, are coupled through the cable 20 for image processing and display by the ultrasound system 30. The cable 20 will also convey control information from the system controller 38 which commands the beamformer as to the specifics of the image being scanned. This control information can be conveyed by a serial digital line in the cable and the information stored in beamformer registers as discussed below. The cable will also carry supply voltages for the beamformer and the transducer array. Even when the transmit/receive beamformer 16 is a digital beamformer producing multibit digital data, the number of cable conductors is still substantially reduced as compared to the conductors required for a conventional 64, 96 or 128 element transducer array.

Since the received ultrasound beam is formed in the probe 10 in FIG. 2, the probe does not need to use the beamformer 32 in the ultrasound system 30. The beamformed echo signals produced by the probe 10 can be coupled directly to the image processor 34 for immediate processing and subsequent display. In the embodiment of FIG. 2 this is accomplished by a switch S which is switched under control of the system controller to connect the beamformed echo signals from probe 10 to the image processor, rather than signals produced by the system beamformer 32. As is conventional, a "personality chip" in the probe 10 or its system connector 22 notifies the user of the characteristics of the probe 10 and selection of probe 10 by the user at the user controls causes the system controller to command the probe to operate and connect its echo information to the image processor 34.

Figure 3:
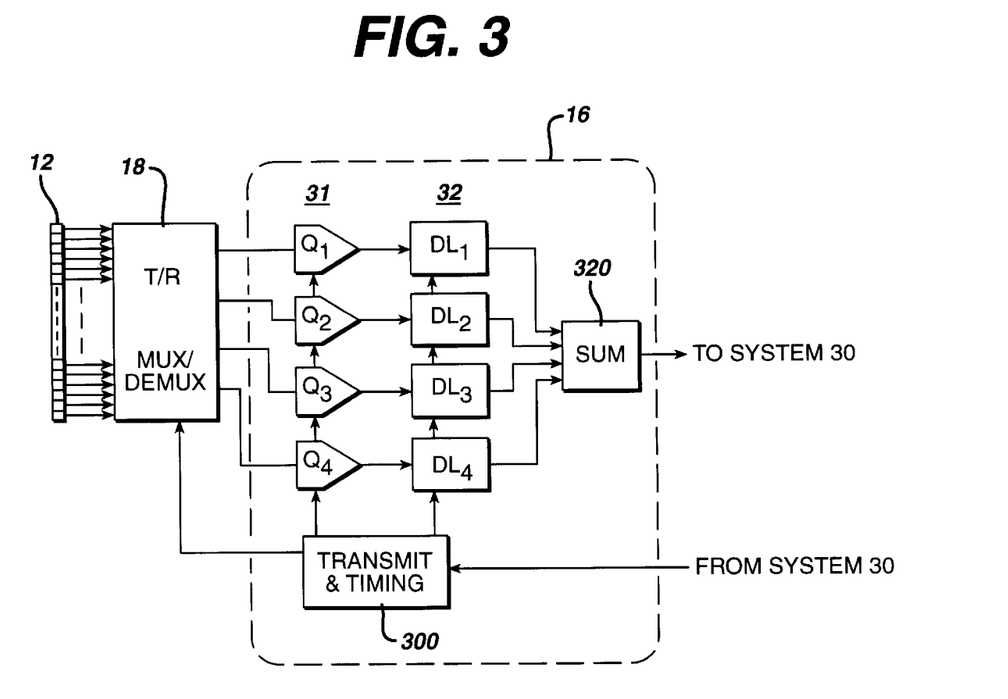
FIG. 3 is a more detailed block diagram of the ultrasonic probe of FIG. 2.

FIG. 3 illustrates an embodiment of an ultrasonic probe with a beamformer 16 and a transmit/receive multiplexer/demultiplexer 18. The beamformer 16 includes transmit and timing circuitry 300 which controls the timing of the ultrasonic waves transmitted by the elements of the transducer array 12. The transmit and timing circuitry receives command signals from the ultrasound system 30 to control the probe to produce the type of image desired by the user. The transmit and timing circuitry also directs the transmit/receive multiplexer/demultiplexer to select the desired active aperture of the array. The transmit and timing circuitry can also control the nature of the transmitted wave, for instance, transmitting different waves for B mode and Doppler imaging. The timing and control signals are applied to the multiplexer/demultiplexer 18 and elements of the array are excited at the proper times to steer and focus the desired transmit beam.

Echoes received by the array elements are converted to electrical signals by the elements and directed by the multiplexer/demultiplexer 18 to the receive beamforming circuitry of the beamformer 16. The received echo signals from the transducer elements of the active receive aperture are coupled to individual channels of the beamformer; the drawing of FIG. 3 illustrates a four channel beamformer. The preferred beamformer is fabricated in integrated circuit form and preferably will contain a multiple of four channels in each beamformer chip. Four, eight, or sixteen channel beamformer chips may readily be employed for most large element count arrays. The preferred beamformer is a sampled data beamformer which may use either sampled analog or digital technology. In either case each channel of the beamformer includes an initial quantizing stage 31 followed by a delay line stage 32. The outputs of the delay line stages are coupled to a summing circuit 320 which combines the delayed echo signals to form the receive beam. The four channel beamformer illustrated in FIG. 3 includes four quantizing stages $Q_1$, $Q_2$, $Q_3$, and $Q_4$ followed by four delay line stages $DL_1$, $DL_2$, $DL_3$, and $DL_4$. The coherent echo signals at the output of the summing circuit 320 are coupled to the ultrasound system 30 for image processing and display.

When the receive beamformer is of the sampled analog variety the quantizing stages comprise sample-and-hold circuits which sample the received echo signals at times indicated by the transmit and timing circuitry 300. The sampled analog signal voltages are then appropriately delayed by charge coupled device (CCD) bucket brigade delay lines as the delay line stages. The delay time is controlled by the transmit and timing circuitry 300 in any of several ways. One is to select one of a plurality of input taps to the CCD delay line to which the sampled voltage is applied. Another is to select one of a plurality of output taps from the stages of the CCD delay line to the summing circuit 320. In either case the selection of the tap will select the number of stages through which the voltage sample will be shifted and hence delayed. A third delay technique is to vary the frequency at which samples are shifted through the CCD stages: a lower frequency imparts a longer delay to the samples being shifted. The summed output signals may be digitized by an analog to digital converter in the probe and transmitted to the ultrasound system 30 in digital form, or the analog signals may be transmitted to the ultrasound system 30 and converted into digital echo samples in the ultrasound system. The latter approach would require only a single output signal conductor in the cable 20.

When the receive beamformer is a digital beamformer, the quantizing stages comprise analog to digital converters which convert the per element analog signals to digital samples at sampling times indicated by the transmit and timing circuitry 300. The digital echo samples are then digitally delayed by a digital delay line which can take the form of a random access memory, shift register, or digital FIFO register. The delay of each digital delay stage is controlled by the transmit and timing circuitry 300 which controls the write-read interval of a sample in memory or the shift frequency of a shift register or FIFO register. The delayed samples at the outputs of the digital delay lines are digitally summed and forwarded to the ultrasound system 30.

Figure 4:
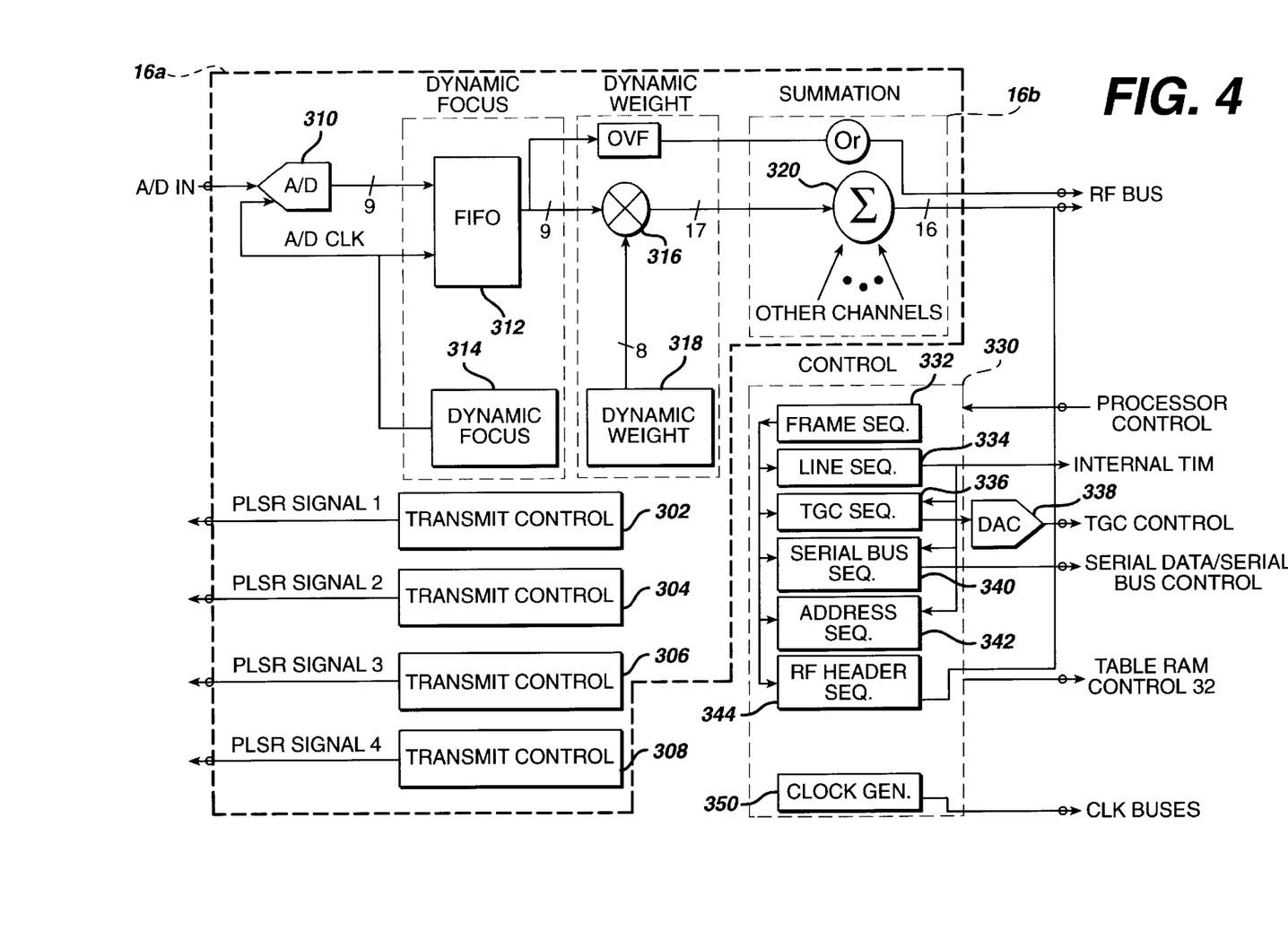
FIG. 4 illustrates in block diagram form a digital beamforming integrated circuit suitable for use in the ultrasonic probe of FIG. 3.

A digital beamformer suitable for use in the probe of FIG. 3 is shown in block diagram form in FIG. 4. This drawing shows one section 16a of a beamformer integrated circuit 16. There are eight such sections on the beamformer I.C. to provide beamforming of the signals of eight transducer elements from the multiplexer/demultiplexer 18. Each echo signal from the multiplexer/demultiplexer is coupled to the input of an A/D converter 310, where the echo signals are converted to digital data. The A/D converters are located on the same integrated circuit as the beamformer itself, which minimizes the external connection pins of the integrated circuit. only one analog input pin is required for each beamformer channel, and only one set of digital output pins is required for the coherently summed output signal. The digital data from the A/D converter for each element (or each pair or group of elements in a folded or coarse aperture) is shifted into a first in, first out (FIFO) register 312 by a clock signal A/D CLK. The A/D CLK signal is provided by a dynamic focus controller 314 which defers the start of the clock signal to provide an initial delay, then controls the signal sampling times to provide dynamic focusing of the received echo signals. The length of the FIFO register 312 is determined by the transducer center frequency, the aperture size, the curvature of the array, and the beam steering requirement. A higher center frequency and a curved array will reduce the steering delay requirement and hence the length of the FIFO register, for instance. The delayed echo signals from the FIFO register 312 are coupled to a multiplier 316 where the echo signals are weighted by dynamic weight values provided by a dynamic weight controller 318. The dynamic weight values weight the echo signals in consideration of the effects of the number of active elements, the position of an element in the aperture, and the desired apodization function, as the aperture expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade through a summer 320. The beamformed echo signals, together with synchronous overflow bits, are produced as output scanline data on an RF data bus. Accompanying each sequence of scanline echo signals is identifying information provided by an RF header sequencer on the I.C., which identifies the type of scanline data being produced. The RF header can identify the scanline as B mode echo data or Doppler data, for instance.

Other digital and sampled data storage devices can be used to provide the beamformer delays, if desired. A dual ported random access memory can be used to store the received digital echo samples, which are then read out from the memory at times or in sequences which provide the desired delay for the signals from the transducer elements.

Each section 16a of the beamformer I.C. includes transmit control circuits 302–308 for four transducer elements of the array. The eight sections of the I.C. thus provide transmit control for 32 elements of the array at the same time, thereby determining the maximum transmit aperture. The transmit control circuits produce waveforms of predetermined durations and periodicities which activate multiplexer pulsers at the appropriate times to produce a transmitted acoustic signal which is steered in the desired direction and focused at the desired depth of focus.

The beamformer I.C. 16 includes a common control section 330 which provides overall control for the transmission and receive functions of the eight beamformer channels on the I.C. The control section 330 is controlled by and receives data under control of the system controller 38 located in the ultrasound system 30. The control data tables for a particular image frame are stored in memory in the ultrasound system and are loaded into the control section 330 under command of the system controller. The control section 330 includes a number of sequencers for the probe's transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the timing required to acquire the desired scanlines. During the scanline acquisition the line sequencer controls the TGC sequencer 336 so that it will produce the desired sequence of TGC control data. The TGC control data from the TGC sequencer is converted to a voltage signal by a digital to analog converter (DAC) 338 and applied to the TGC control input terminal(s) of the multiplexer/demultiplexer 18. The address sequencer 342 controls the loading of data for a new scanline into various realtime registers of the beamformer such as the registers of the TGC sequencer, the dynamic focus 314 and dynamic weight controllers 318, and the serial bus sequencer 340, which produces serial data on a serial bus for control registers of the multiplexer/demultiplexer 18. All registers on the beamformer I.C. which perform real time functions are double buffered. The registers of the transmit/receive multiplexer/demultiplexer 18 are also double buffered so that control data for multiplexing and TGC control can be put on the serial bus and loaded into multiplexer/demultiplexer registers during the line preceding the scanline for which the control data is used.

The beamformer I.C. includes in its control section a clock generator 350 which produces a plurality of synchronous clock signals from which all operations of the probe are synchronized. A crystal oscillator (not shown) is coupled to the beamformer I.C. 16 to provide a basic high frequency such as 60 MHz from which all of the clock signals of the probe may be derived.

Further details on the operation of the beamformer I.C. and its sequencers may be found in U.S. Pat. No. 5,817,024.

Figure 5:
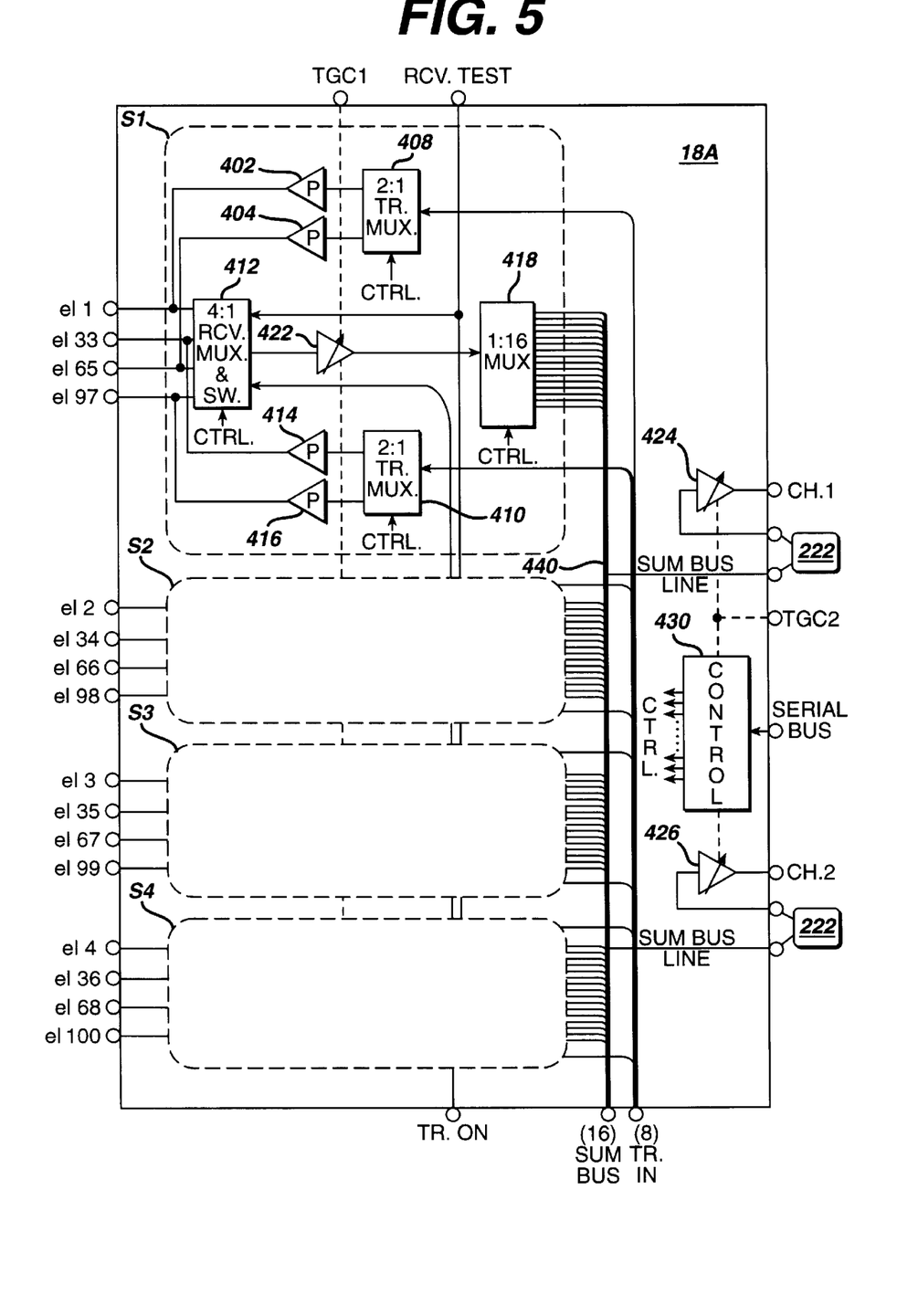
FIG. 5 illustrates in block diagram form a multiplexer suitable for use in the ultrasonic probe of FIG. 3.

A transmit/receive multiplexer I.C., suitable for use as multiplexer/demultiplexer 18 in the probe of FIG. 3, is shown in FIG. 5. The signal paths of the multiplexer I.C. 18A are divided into four identical sections S1, S2, S3, and S4. In this drawing section S1 is shown in internal detail. The section S1 includes two 2:1 transmit multiplexers 408 and 410, each of which is responsive to a pulser signal on one of eight Transmit In lines. Each 2:1 transmit multiplexer has two outputs which drive pulsers 402, 404, and 414, 416, the outputs of which are coupled to multiplexer I.C. pins to which transducer elements are connected. In the illustrated embodiment the 2:1 transmit multiplexer 408 is coupled to drive either element 1 or element 65, and the 2:1 transmit multiplexer 410 is coupled to drive either element 33 or element 97. The 2:1 transmit multiplexers of the other sections of the multiplexer I.C. 18A are each similarly coupled to four transducer elements. With a separate pulser for each transducer element, the multiplexer I.C. 18A can independently and simultaneously drive eight of the sixteen transducer elements to which it is connected.

The transducer element pins to which the pulsers of each section are coupled are also coupled to the inputs of a 4:1 receive multiplexer and switch 412. When the pulsers are driving the transducer elements during ultrasound transmission, a signal on a Transmit On line which is coupled to all of the 4:1 Receive Multiplexers and Switches on the multiplexer I.C. switches them all into a state which presents a high impedance to the high voltage drive pulses, thereby insulating the rest of the receive signal paths from these high voltage pulses. All of the 4:1 receive multiplexers and switches of the multiplexer I.C. are also coupled to a Receive Test pin of the multiplexer I.C., by which a test signal can be injected into the receive signal paths and propagate through the receiver system. During echo reception each 4:1 receive multiplexer and switch couples the signals of one of the four transducer elements to which it is coupled to a 1:16 multiplexer 418 by way of a first TGC stage 422. The gain of the first TGC stages on the multiplexer I.C. is controlled by a voltage applied to a TGC1 pin of the multiplexer I.C. which, in a constructed embodiment, comprises two pins for application of a differential control voltage. The 1:16 multiplexers of each section of the multiplexer I.C. each route received echo signals to one of the sixteen lines of a Sum Bus 440. Two of the sixteen Sum Bus lines are shown at the right side of the drawing, and are coupled to filter circuits 222. The filtered bus signals are coupled to input pins leading to two second TGC stages 424 and 426, the gain of which is controlled by the voltage applied to one or two TGC2 pins. The outputs of these second TGC stages in the illustrated embodiment are connected to output pins leading to channels of the probe's beamformer I.C.

The multiplexer I.C. 18A also includes a control register 430 which receives control signals over a serial bus from the beamformer I.C. The control register distributes control signals to all of the multiplexers of the multiplexer I.C. as shown by the Ctrl. input arrows.

Constructed embodiments of the multiplexer and beamformer I.C.s will have a number of pins for supply and bias voltages and ground connections and are not shown in the drawings.

It will be appreciated that only a few conductors are needed in the probe cable in the embodiments of FIGS. 2–5 since the numerous conductors for individual transducer elements are replaced by conductors for the beamformer control data, the beamformed output signals and supply voltages for the transducer, beamformer and multiplexer I.C.s. A typical CCD embodiment can require a conductor for the CCD beamformer output signals, a serial data line providing control data from the ultrasound system to the transmit and timing circuitry 300, DC supply voltages and reference conductors for the beamformer and multiplexer I.C.s, and a drive voltage as required to drive the piezoelectric material during ultrasound transmission. The digital beamformer embodiment would replace the CCD output conductor with a number of conductors equal to the number of bits in a beamformed data word (for parallel transmission) or a serial data line if the beamformed words are being sent to the ultrasound system as serial data. Parallel output data, while requiring more conductors in the cable, affords a worthwhile improvement in axial resolution and eliminates the need for a serial to parallel converter in the ultrasound system.

The present inventors have discovered that since an ultrasound probe of the present invention is producing beamformed scanline samples as output signals rather than individual signals from a large number of transducer elements, the volume of data produced by the probe is at a level which will permit wireless transmission of the probe's output signals to the ultrasound system. A transmitter bandwidth of 4 M bits per second is sufficient to transfer ultrasound images without compression at a frame rate of nearly 15 Hz, suitable for real time image display. I.C. transmitter bandwidths today are in the range of 11 MBPS, and are expected to be in the range of 25 MBPS in a few years. Additionally, by the use of data compression, the number of bits per B mode ultrasound image, around 250, 000 bits per image, can be reduced with minimal decrease in image quality by data compression factors ranging from 4 to 20, affording greater frame rates. An embodiment of the present invention which provides this cable-less connection to an ultrasound system is shown in FIGS. 6a and 6b.

Figure 6A:
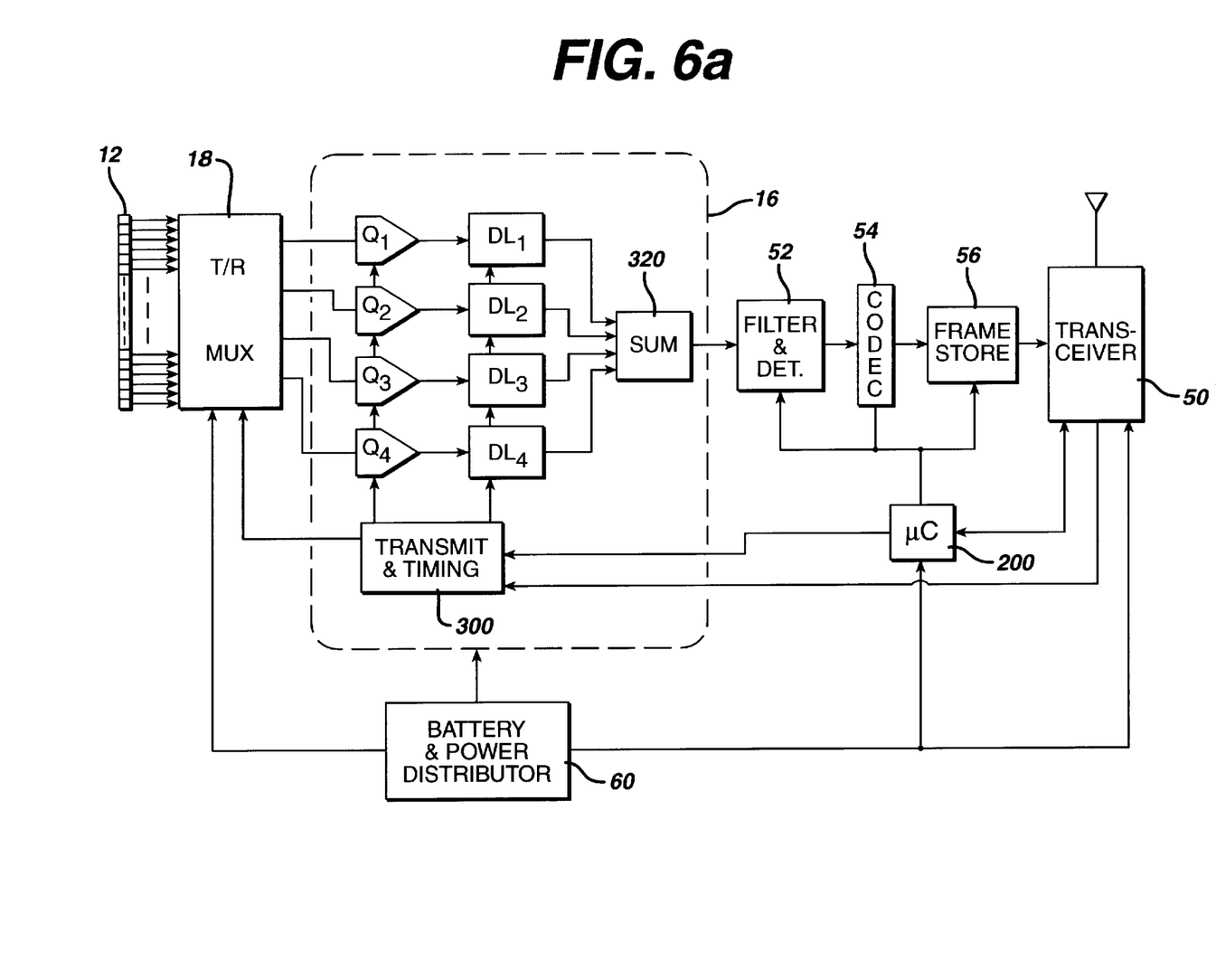
FIGS. 6a and 6b illustrate a cable-less embodiment of the ultrasonic probe of FIG. 3 and an ultrasonic imaging system in accordance with the principles of the present invention.
Figure 6B:
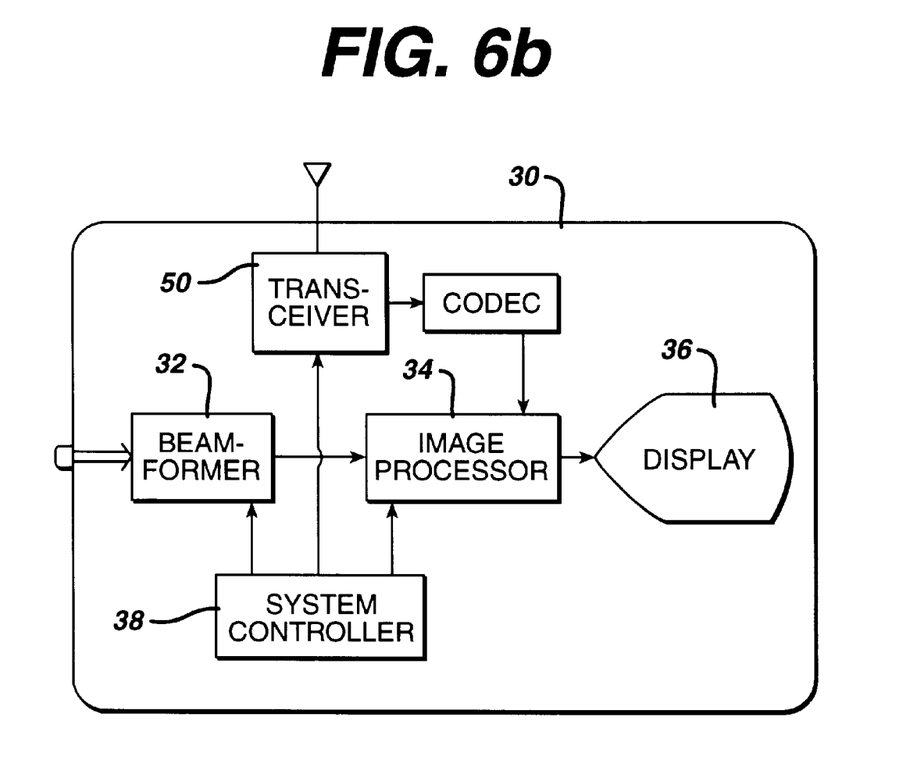

In FIG. 6a the probe of FIG. 3 includes several additional elements coupled to the beamformer 16, a digital signal processor 52 which performs filtering and detection, a compression/decompression circuit (CODEC 54) which compresses the beamformed data, a double buffered frame store 56, and a transceiver 50 which communicates with a similar transceiver in the ultrasound system 30. The CODEC 54 is capable of implementing several compression schemes, including JPEG, MPEG and wavelet compression techniques, as described in concurrently filed U.S. patent application Ser. No. 09/197,398, entitled "ULTRASONIC DIAGNOSTIC IMAGING SYSTEM WITH CORDLESS SCANHEADS." The elements 50–56 are operated under control of a microcontroller 200 which controls the processing and transmission of data to and from the ultrasound system. Useful as microcontrollers are processors such as the Intel 80186 processor and comparable contemporary processors available from vendors such as Hitachi and Intel. The transceiver 50 receives control data from the ultrasound system to control the type of ultrasound image being produced, such as a B mode or Doppler image, and the size of a Doppler window in a colorflow image, for instance. As this control data is received it is coupled to the transmit and timing circuitry 300 to control the scanning performed by the probe.

The scanline data produced by the summer 320 is coupled to the digital signal processor 52 which performs filtering and, optionally, detection. The DSP 52 can also perform Doppler processing as described in the aforementioned U.S. Pat. No. 5,817,024. The filtering performed can be either lowpass or bandpass filtering which removes sampling frequency signal components from the beamformed signals. Preferably this filtering is implemented by multiplier-accumulators performing quadrature bandpass filtering (QBPs). As described in U.S. patent application Ser. No. 08/893,426, such an implementation advantageously performs three functions: bandlimiting the beamformed signals, separating the signals into quadrature (I and Q) pairs, and decimating the sampling rate. In a preferred embodiment the transducer signals are oversampled by the quantizing stages of the beamformer in relation to the Nyquist criterion. oversampling permits the filtering of the beamformed signals by decimation filtering which both imposes a filter characteristic on the signals and reduces the data rate. The reduced data rate has the benefit of lessening the data transfer requirement for the transceiver in a wireless probe.

B mode signals can be detected in the DSP by taking the square root of the sum of the squares of the I and Q samples. For Doppler signals the I and Q data can be wall filtered by the DSP and, through storage of a group of received scanlines forming a Doppler ensemble, Doppler frequency estimation can be performed at sample volume points along each scanline. The ultrasound signal data may be compressed if desired by the CODEC 54 and is stored temporarily in the frame store 56. At the time when the microcontroller 200 determines that the ultrasound data is to be transmitted to the ultrasound system 30, the data is coupled to the transceiver 50 for transmission back to the ultrasound system for image processing and display. Since image processing including scan conversion is performed in the ultrasound system, the scanlines are transmitted to the ultrasound system in unscanconverted form, e.g., R-θ format. The image processor 34 in the ultrasound system converts the R-θ scanline data to the desired display format.

Since the cable-less probe of FIG. 6a does not receive power by the usual cable, the probe must be battery powered. A battery and power distributor subsystem 60 is shown as a component of the probe. The subsystem 60 preferably uses rechargeable lithium ion batteries and produces supply voltages for the circuitry and transceiver of the probe and the requisite excitation voltage for the piezoelectric elements of the transducer array.

The ultrasound system 30 of FIG. 6b includes a transceiver 50 for the transmission of scan control data to the probe of FIG. 6a and for the reception of ultrasonic image data from the probe. The scan control data is provided to the system transceiver 50 by the system controller 38. The received image data bypasses the beamformer 32 in the ultrasound system since it has already been beamformed in the probe, and is applied directly to the image processor 34 for image processing and display.

Transceiver configurations suitable for use in the probe of FIG. 6a are described in concurrently filed U.S. patent application Ser. No. 09/197,398, entitled "ULTRASONIC DIAGNOSTIC IMAGING SYSTEM WITH CORDLESS SCANHEADS."

The ultrasonic image data that is transmitted from the probe to the ultrasound system can be transmitted in packets, or blocks of data, which are preceded and followed by headers and trailers providing information concerning the characteristics of the ultrasound data. Preferably the transmitted data is grouped into sequences of scanline data, and a plurality of scanlines for an image frame are transmitted in a sequence which is preceded and followed by frame headers and trailers. The transmitted data may also be accompanied by communication protocol headers and trailers identifying the transmission format. The header information may include information identifying the probe, the type of compression employed in the transmission, and operating data such as probe temperature and other safety information. Such formatting protocols for a cordless scanhead are described more fully in concurrently filed application Ser. No. 09,197,186, entitled "ULTRASONIC DIAGNOSTIC IMAGING WITH CORDLESS SCANHEAD TRANSMISSION SYSTEM."

Figure 8A:
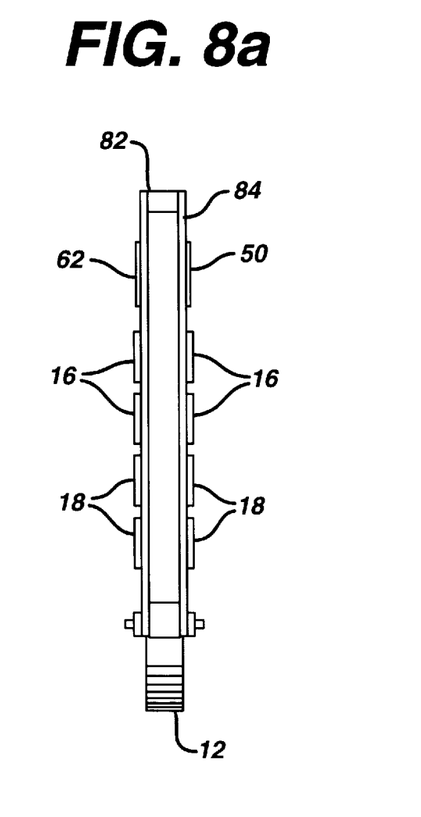
FIGS. 8a and 8b illustrate the internal array and integrated circuit packaging of a cable-less probe.
Figure 8B:
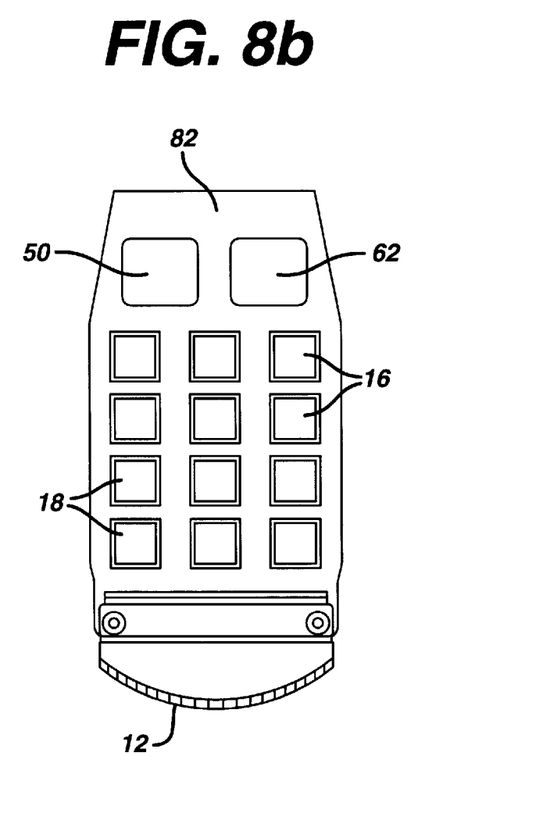

Assembly drawings for a cordless ultrasound probe are shown in FIGS. 8a, 8b, and 9a–9d. FIGS. 8a and 8b are side and plan views, respectively, of the inner components of a cordless ultrasound probe. Two printed circuit boards 82 and 84 are connected in a parallel sandwich arrangement as shown in FIG. 8a. The integrated circuits 18 for the multiplexer and for the beamformer 16 are mounted on the printed circuit boards. A transducer array module 12 is mounted at one end of the printed circuit boards and the elements of the array are connected to the multiplexer I.C.s. The number of multiplexer and beamformer I.C.s used will be determined by the number of elements of the transducer array and the desired active aperture during transmission and reception. For example, eight multiplexer I.C.s may be used for a 128 element array when each multiplexer I.C. is capable of connecting to sixteen elements as is the multiplexer I.C. of FIG. 5. Eight beamformer I.C.s, each with eight receive channels, may be used when a 64 channel receive beamformer is desired. Behind the multiplexer and beamformer I.C.s in FIG. 8b are the transceiver and power distribution circuits 50 and 62.

Figure 9A:
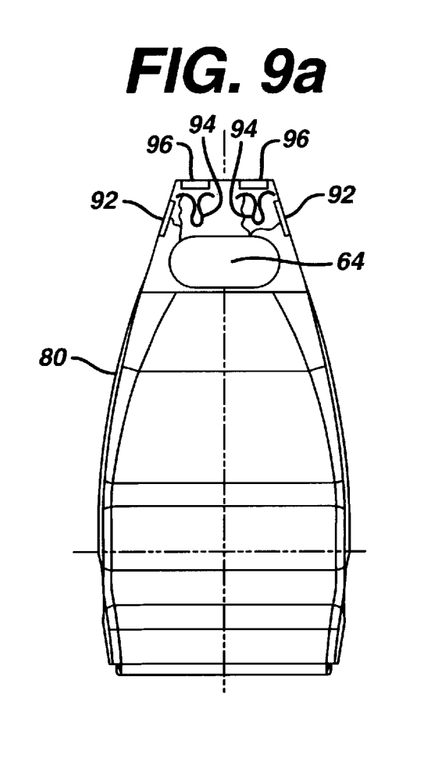
FIGS. 9a–9d illustrate the probe case for the components of FIGS. 8a and 8b, including the battery charging circuitry.

The assembled printed circuit boards and transducer module are mounted in a case 80, one half of which is shown in FIG. 9a. The lower end of the case in the drawing has a separate cap piece (not shown) which fits over the transducer array module and forms an acoustic window in front of the array. The printed circuit board is connected to a battery 64 which is located in the upper end (back) of the case 80. The terminals of the battery 64 are connected to external charging contacts 92 which are flush mounted on each side of the case 80 as shown in the plan view of FIG. 9a and the side view of FIG. 9b. Alternatively, the probe may employ internal charging contacts, here shown as spring contacts 94 in FIG. 9a. Access to the spring contacts may be by a movable cover or door over each spring contact, but in FIGS. 9a and 9b access to the spring contacts is provided by two rubber gaskets 96, one of which is shown in FIG. 9d. Each gasket has a self-sealing slit 98 through which battery charging pins may be inserted to access the spring contacts 94.

Figure 7:
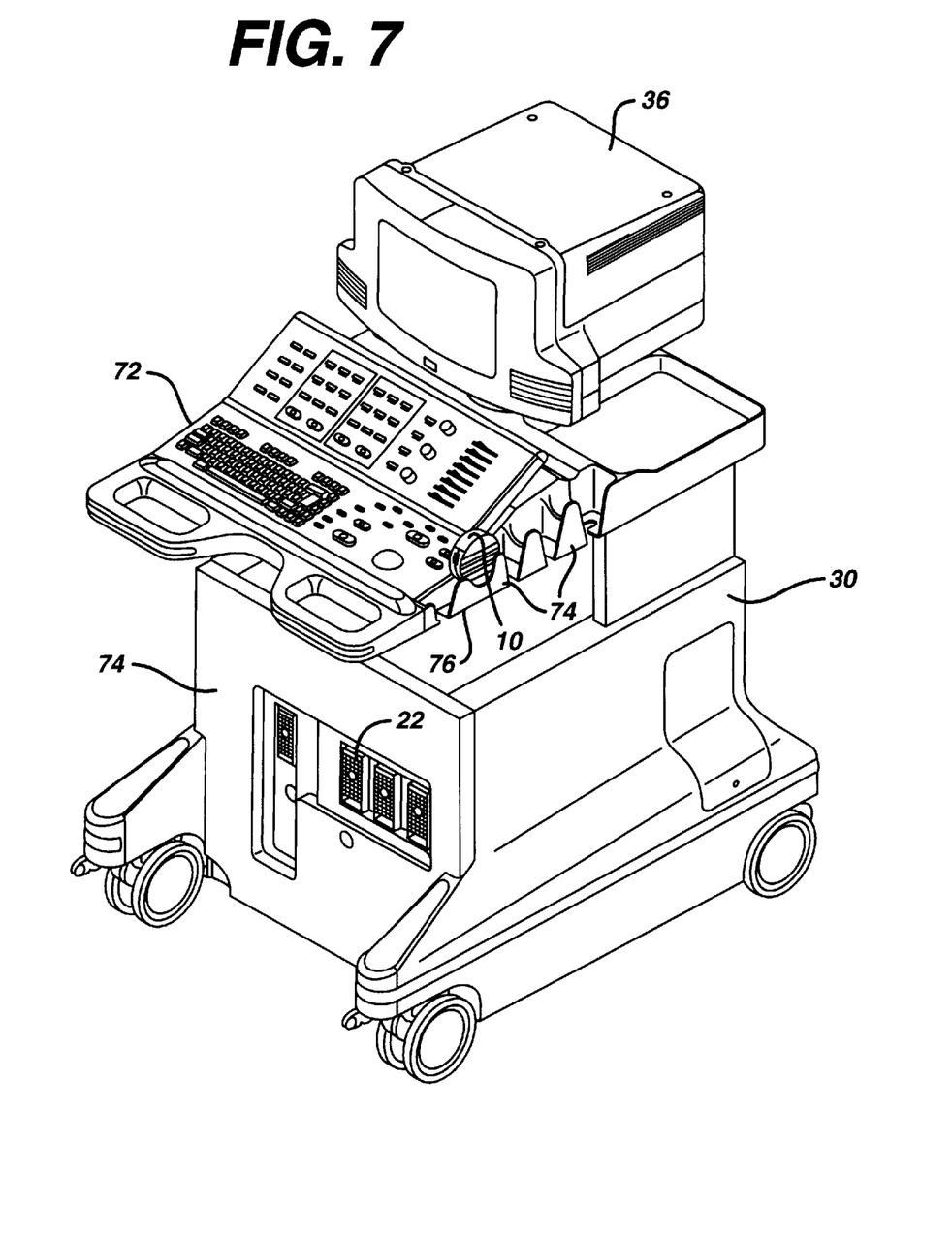
FIG. 7 illustrates an ultrasonic imaging system with a probe holder for a cable-less probe.

Since the cordless probe of FIG. 6a and FIGS. 8–9 uses a rechargeable battery, provision must be made to recharge the probe battery in a way which is convenient for the user. FIG. 7 illustrates an a.c.-powered cart-borne ultrasound system 30. The lower portion 74 of the system 30 includes a power supply and circuit boards by which the system processes and displays ultrasound signals. A number of connectors are shown on the front of this lower portion 74, including a connector 22 for the cable 20 of the probe 10 of FIG. 2. Located on top of the lower portion 74 is a user interface 72 containing the system controls by which a user operates and controls the ultrasound system. Above the user interface is a display monitor 36 on which the ultrasound images produced by the system 30 are displayed.

Figure 10:
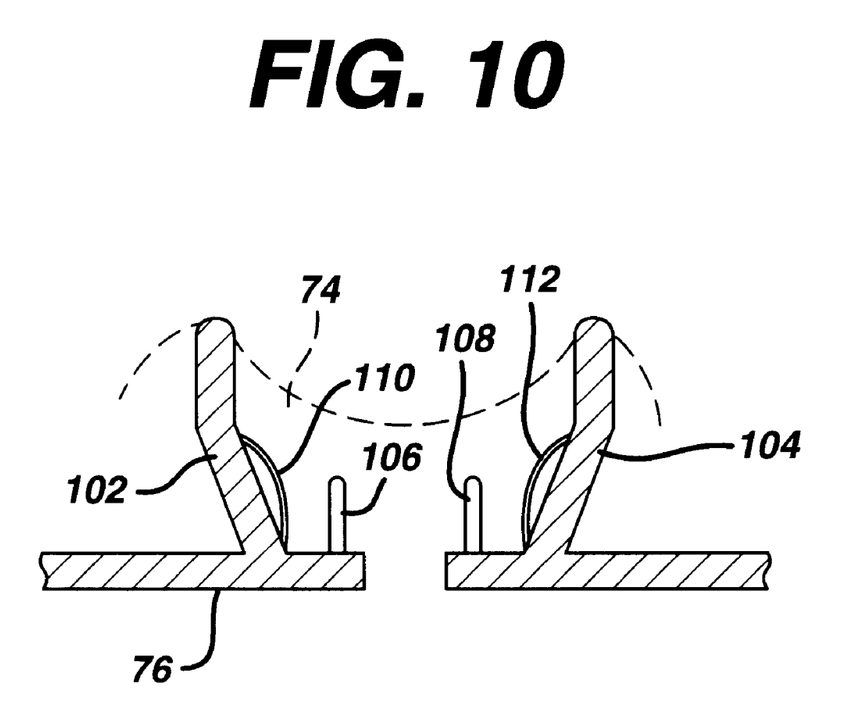
FIG. 10 illustrates a probe holder with a battery charger for use with the cable-less probe of FIGS. 7–9.

Located to the right of the user interface 72 is an integral probe holder 74. Conventionally, probes with cables connected to the connectors 22 would be hung in the probe holder 74 when not being used. However the probe holder 74 in FIG. 7 includes a special holder for holding and recharging a cordless ultrasound probe 10 as shown in the drawing. The recharging probe holder is shown in cross-section in FIG. 10. The probe holder includes a base 76 and two support pieces 102 and 104. The support pieces are contoured to engage the contour of the probe case 80. Within the enclosure formed by the base and support pieces are charging contacts 106,108 or 110,112. These charging contacts are electrically connected to a source of charging current provided by the system's power supply which is located in the lower portion 74 of the ultrasound system. When the cordless probe utilizes the external charging contacts 92 these contacts will, when the back of the probe is inserted between the support pieces 102,104, engage the spring-like charging contacts 110,112. Thus, whenever the cordless probe 10 is unused and placed in the probe holder 74, its battery will be recharged by the ultrasound system.

Ultrasound probes operate in a difficult environment for rechargeable items, since the probes are virtually always used with acoustic couplant. Acoustic coupling gel is spread on the patient or over the transducer to form an acoustic pathway between the probe and the patient's body. This gel can contaminate the external charging contacts 92 and 110,112 of the probe and probe holder, and must continually be wiped from the probe and these contacts. The gel can also form pathways for discharging the battery, which must be prevented. The alternative charging approach shown in FIG. 9a, the use of the internal spring contacts 94, protects the probe's charging contacts from excessive gel contamination by locating the contacts inside the probe case. When a cordless probe with this form of charging system is inserted into the probe holder 74, the rod-like charging contacts 106,108 penetrate the slits 98 in the gaskets 96 to engage the probe's internal spring contacts 94. As the contacts 106,108 force their way through the slits in the gaskets, a wiping action takes place to wipe away any excessive gel on the contacts 106,108, leaving the gel on the outside of the probe.

Only occasional maintenance is needed in this embodiment to remove any buildup of gel which may have accumulated over time around the spring contacts 94.

Figure 9B:
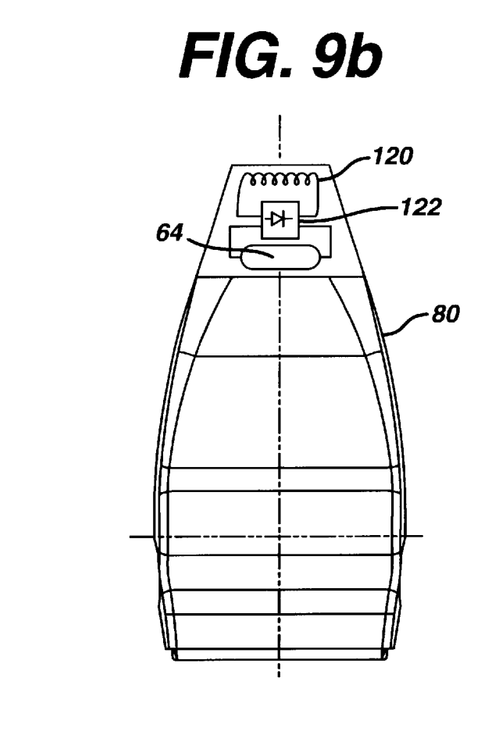
Figure 9C:
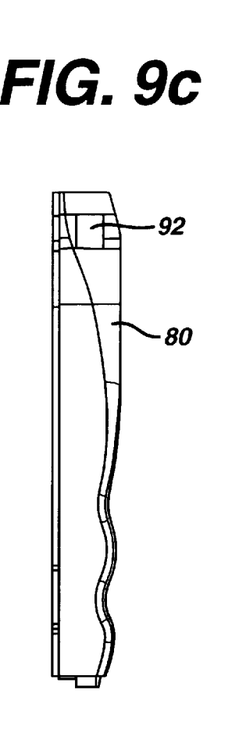
Figure 9D:
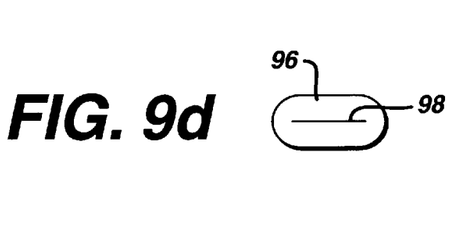

Yet a third approach to energizing the probe is shown in FIG. 9*b*. In this embodiment power from a charging circuit on the ultrasound system cart or separately located is inductively coupled to a coil 120 which is fully enclosed within the probe case 80. The energy received by the coil 120 is rectified by a rectifier 122 and coupled to charge the battery 64. Since this inductive charging technique requires no physical contact with electrical components of the probe and hence no access to the interior of the probe, contamination of the probe circuitry by gels is completely avoided.

What is claimed is:

1. An ultrasonic diagnostic imaging system including an a.c.-powered ultrasound system which receives ultrasound signals from an ultrasound probe and processes and displays said received signals, and an ultrasound probe comprising:

an ultrasound probe which wirelessly transmits ultrasound image signals to said ultrasound system and which includes a rechargeable battery; and a probe holder, located on said ultrasound system, which holds and recharges said ultrasound probe when said probe is not in use for scanning.

2. The ultrasonic diagnostic imaging system of claim 1, wherein said probe holder includes an electrical contact coupled to a source of energizing potential and said ultrasound probe includes an electrical contact coupled to said battery.

3. The ultrasonic diagnostic imaging system of claim 2, wherein said ultrasound probe electrical contact is protected from excessive exposure to ultrasound gel.

4. The ultrasonic diagnostic imaging system of claim 3, wherein said ultrasound probe electrical contact is protected by a gasket.

5. The ultrasonic diagnostic imaging system of claim 1, wherein said probe holder includes a source of energizing potential and said ultrasound probe includes a receiver, coupled to said battery, which receives battery recharging energy from said energizing potential.

6. The ultrasonic diagnostic imaging system of claim 5, wherein said source of energizing potential is inductively coupled to said probe receiver.

7. An ultrasonic diagnostic imaging system including an ultrasound system which receives ultrasound signals from an ultrasound probe and processes and displays said received signals, and an ultrasound probe comprising:

a probe enclosure;

a transmitter, located in said enclosure, which wirelessly transmits ultrasound signals to said ultrasound system;

a rechargeable battery; and charging contacts, coupled to said rechargeable battery, for applying charging potential to said battery; and a protective cover which protects said charging contacts from contaminants when said probe is being used for scanning.

8. The ultrasonic diagnostic imaging system of claim 7, wherein said protective cover comprises a gasket.

9. The ultrasonic diagnostic imaging system of claim 8, wherein said ultrasound system includes a source of energizing potential for charging said probe battery, wherein said source of energizing potential is admitted through said gasket to recharge said probe battery.

10. The ultrasonic diagnostic imaging system of claim 7, wherein said charging contacts comprise spring contacts.

11. An ultrasonic diagnostic imaging system including an ultrasound system which receives ultrasound signals from an ultrasound probe and processes and displays said received signals, and an ultrasound probe comprising:

a probe enclosure;

a transmitter, located in said enclosure, which wirelessly transmits ultrasound signals to said ultrasound system;

a rechargeable battery; and an inductor, coupled to said rechargeable battery, for applying charging potential to said battery.

12. The ultrasonic diagnostic imaging system of claim 11, wherein said battery and said inductor are located in said enclosure.

13. The ultrasonic diagnostic imaging system of claim 11, wherein said ultrasound system includes a source of energizing potential for charging said probe battery, wherein said energizing potential is inductively coupled to said probe inductor.

14. The ultrasonic diagnostic imaging system of claim 11, further comprising a rectifier coupled to said battery and said inductor for rectifying said charging potential.

\* \* \* \* \*